United States Patent [19]

Lamm et al.

[11] Patent Number: 5,739,343
[45] Date of Patent: Apr. 14, 1998

[54] NITRO DYES

[75] Inventors: Gunther Lamm, Hassloch; Helmut Reichelt, Neustadt; Clemens Grund, Mannheim, all of Germany

[73] Assignee: BASF Aktiengesellschaft, Ludwigshafen, Germany

[21] Appl. No.: 776,055

[22] PCT Filed: Jul. 13, 1995

[86] PCT No.: PCT/EP95/02745

§ 371 Date: Jan. 21, 1997

§ 102(e) Date: Jan. 21, 1997

[87] PCT Pub. No.: WO96/03463

PCT Pub. Date: Feb. 8, 1996

[30] Foreign Application Priority Data

Jul. 21, 1994 [DE] Germany ............................ 44 25 794.5

[51] Int. Cl.[6] ...................... C09B 51/00; C07D 271/06
[52] U.S. Cl. .................................... 548/131; 8/649
[58] Field of Search .......................... 548/131; 8/649

[56] References Cited

U.S. PATENT DOCUMENTS 2,708,149 5/1955 Kartinos et al. .
3,957,777 5/1976 Toth ............................. 260/247.7

FOREIGN PATENT DOCUMENTS

| A 0 006 171 | 1/1980 | European Pat. Off. . |
| A 0 037 465 | 10/1981 | European Pat. Off. . |
| A 2 133 803 | 12/1972 | France . |
| A 2 451 932 | 10/1980 | France . |
| 1535 401 | 12/1978 | United Kingdom . |
| A 89 10384 | 11/1989 | WIPO . |

OTHER PUBLICATIONS

Colour Index, Third Edition, vol. 4 C.I. Disperse Yellow 42 (10338) (no date).
Chemical Abstracts, vol. 76, No. 18, May 1, 1972, p. 84, Columbus, Ohio, US.

*Primary Examiner*—Robert Gerstl
*Attorney, Agent, or Firm*—Oblon, Spivak, McClelland, Maier & Neustadt, P.C.

[57] ABSTRACT

Nitro dyes of the formula

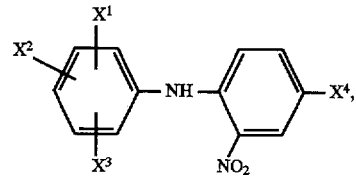

where $X^1$ and $X^2$ are hydrogen, $C_1$–$C_6$-alkyl, $C_1$–$C_6$-alkoxy or pyrrolidin-2-on-1-yl, $X^3$ is hydrogen or $C_1$–$C_6$-alkyl, and $X^4$ is a radical of the formula

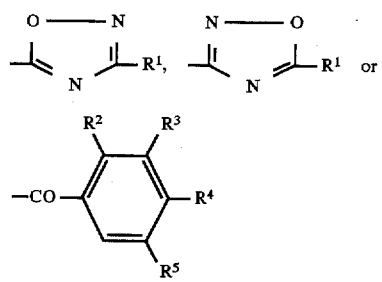

where $R^1$ is hydrogen, substituted or unsubstitued $C_1$–$C_{12}$-alkyl, substituted or unsubstituted $C_3$–$C_7$-cycloalkyl or substituted or unsubstituted phenyl, $R^2$ and $R^3$ are hydrogen, $C_1$–$C_6$-alkyl or $C_1$–$C_6$-alkoxy, $R^4$ is hydrogen, methyl, ethyl, methoxy or ethoxy, and $R^5$ is hydrogen or $C_1$–$C_6$-alkyl, are useful for dyeing or printing textile materials.

9 Claims, No Drawings

NITRO DYES

This application is a 371 of PCT/EP95/02745 filed Jul. 13, 1995. The present invention relates to novel nitro dyes of the formula I

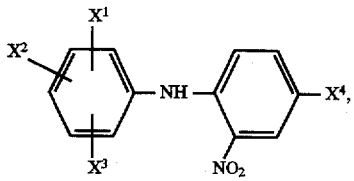

where

X¹ and X² are independently of each other hydrogen, $C_1$–$C_6$-alkyl, $C_1$–$C_6$-alkoxy or pyrrolidin-2-on-1-yl, X³ is hydrogen or $C_1$–$C_6$-alkyl, and X⁴ is a radical of the formula

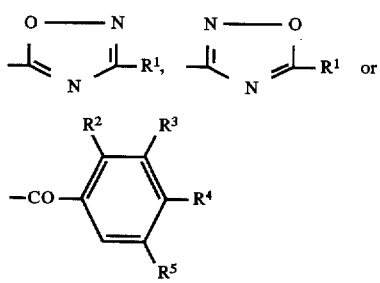

where

R¹ is hydrogen, $C_1$–$C_{12}$-alkyl with or without interruption by from 1 to 3 oxygen atoms in ether function and with or without phenyl, phenoxy or acetyl substitution, $C_3$–$C_7$-cycloalkyl, which may be $C_1$–$C_4$-alkyl-substituted, or phenyl, which may be $C_1$–$C_4$-alkyl-, $C_1$–$C_4$-alkoxy- or halogen-substituted, R² and R³ are independently of each other hydrogen, $C_1$–$C_6$-alkyl or $C_1$–$C_6$-alkoxy, R⁴ is hydrogen, methyl, ethyl, methoxy or ethoxy, and R⁵ is hydrogen or $C_1$–$C_6$-alkyl, processes for their preparation, and their use for dyeing or printing textile materials.

The nitro dye C. I. Disperse Yellow 42 (10338) is commercially available. It comprises 2-nitro-4-phenylsulfamoyldiphenylamine.

It is an object of the present invention to provide novel nitro dyes which have advantageous application properties.

We have found that this object is achieved by the nitro dyes of the formula I defined at the beginning.

Any alkyl appearing in the abovementioned formula can be straight-chain or branched.

In any substituted alkyl or cycloalkyl appearing in the abovementioned formula I the number of substituents is generally 1 or 2.

In any substituted phenyl appearing in the abovementioned formula I the number of substituents is generally from 1 to 3, preferably 1 or 2.

X¹, X², X³, R¹, R², R³ and R⁵ are each for example methyl, ethyl, propyl, isopropyl, butyl, isobutyl, sec-butyl, tert-butyl, pentyl, isopentyl, neopentyl, tert-pentyl, hexyl or 2-methyl-pentyl.

R¹ may also be for example heptyl, octyl, 2-ethylhexyl, isooctyl, nonyl, isononyl, decyl, isodecyl, undecyl or dodecyl (the above designations isooctyl, isononyl and isodecyl are trivial names derived from the oxo process alcohols—cf. Ullmann's Encyclopedia of Industrial Chemistry, 5$^{th}$ Edition, Vol. A1, pages 290 to 293, and also Vol. A10, pages 284 and 285), 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 4,7-dioxaundecyl, 3,6,9-trioxadecyl, 3,6,9-trioxaundecyl, 3,6,9-trioxadodecyl, 4,7,10-trioxaundecyl, benzyl, 1- or 2-phenylethyl, phenoxymethyl, 1- or 2-phenoxyethyl, 2- or 3-phenoxypropyl, acetylmethyl, cyclopropyl, cyclobutyl, cyclopentyl, methylcyclopentyl, dimethylcyclopentyl, cyclohexyl, methylcyclohexyl, dimethylcyclohexyl, cycloheptyl, phenyl, 2-, 3- or 4-methylphenyl, 2,4-dimethylphenyl, 2-, 3- or 4-ethylphenyl, 2,6-diethylphenyl, 2-, 3- or 4-methoxyphenyl, 2,4-dimethoxyphenyl, 2-, 3- or 4-ethoxyphenyl, 2,6-diethoxyphenyl, 2-, 3- or 4-chlorophenyl or 2,4-dichlorophenyl.

X¹, X², R² and R³ may each also be for example methoxy, ethoxy, propoxy, isopropoxy, butoxy, isobutoxy, sec-butoxy, tert-butoxy, pentyloxy, isopentyloxy, neopentyloxy, tert-pentyloxy or hexyloxy.

Preference is given to nitro dyes of the formula I where X¹ and X² are independently of each other hydrogen or $C_1$–$C_4$-alkyl and X³ is hydrogen.

Preference is further given to nitro dyes of the formula I, where X⁴ is a radical of the formula

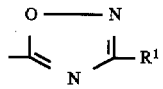

or

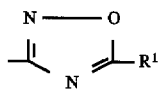

where R¹ is in each case as defined above.

Preference is further given to nitro dyes of the formula Ia

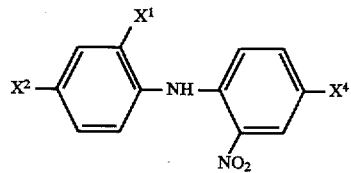

where X¹, X² and X⁴ are each as defined above.

Preference is further given to nitro dyes of the formula I where X⁴ is a radical of the formula

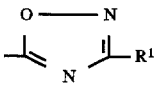

or

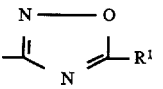

where R¹ is $C_1$–$C_4$-alkyl, cyclohexyl or phenyl.

Particular preference is given to nitro dyes of the formula Ia where $X^1$ and $X^2$ are independently of each other hydrogen or $C_1$–$C_4$-alkyl and $X^4$ is a radical of the formula

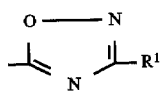

or

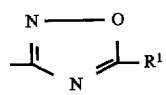

where $R^1$ is $C_1$–$C_4$-alkyl, cyclohexyl or phenyl.

Particular preference is further given to nitro dyes of the formula Ia where $X^1$ and $X^2$ are both hydrogen or both methyl or $X^1$ is hydrogen and $X^2$ is $C_1$–$C_4$-alkyl.

Of particular importance are nitro dyes of the formula Ib or Ic

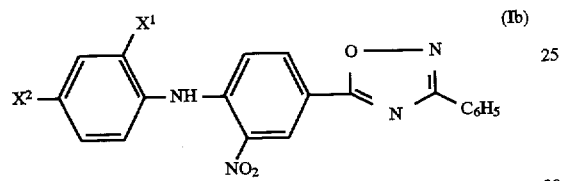 (Ib)

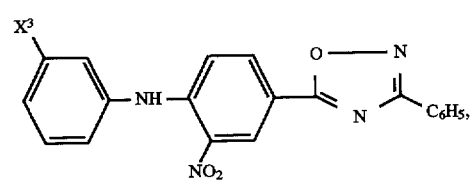 (Ic)

where $X^1$ and $X^2$ are both hydrogen or both methyl or $X^1$ is hydrogen and $X^2$ is $C_1$–$C_4$-alkyl, and $X^3$ is $C_1$–$C_4$-alkyl.

The nitro dyes of the formula I according to the present invention can be obtained in a conventional manner.

For example, a nitrobenzene of the formula II

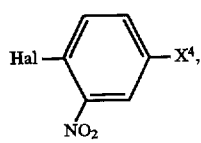 (II)

where Hal is halogen, especially chlorine or bromine, and $X^4$ is as defined above, can be reacted with aniline of the formula III

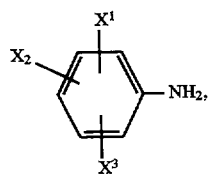 (III)

where $X^1$, $X^2$ and $X^3$ are each as defined above.

Those nitro dyes of the formula I where $X^4$ is a radical of the formula

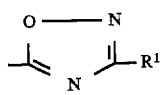

can be obtained for example by reacting a benzoyl halide of the formula IV

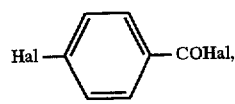 (IV)

where Hal is as defined above, with a compound of the formula V

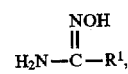 (V)

where $R^1$ is as defined above, to form compounds of the formula VI

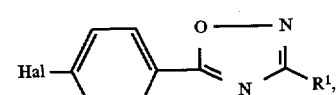 (VI)

where $R^1$ and Hal are each as defined above, nitrating said compounds and then reacting the nitration products with the aniline of the formula III.

Those nitro dyes of the formula I where $X^4$ is a radical of the formula

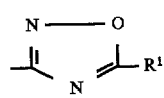

can be obtained for example by reacting a benzamidine of the formula VII

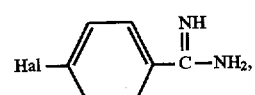 (VII)

where Hal is as defined above, with a carboxylic acid derivative of the formula VIII $R^1$—CO—Z (VIII), where Z is halogen, especially chlorine, $C_1$–$C_6$-alkoxy or a radical of the formula O—CO—$R^1$ and $R^1$ is in each case as defined above, nitrating the resulting compound of the formula IX

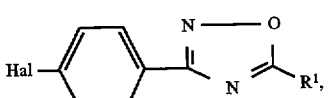 (IX)

where Hal and $R^1$ are each as defined above, and then reacting the nitration product with the aniline of the formula III.

However, in this case it is also possible to start from a cyano compound of the formula X

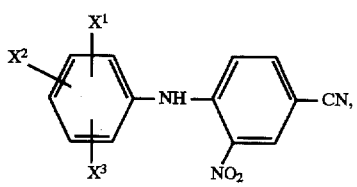

where $X^1$, $X^2$ and $X^3$ are each as defined above, converting it with hydroxylamine into the amide-oxime of the formula XI

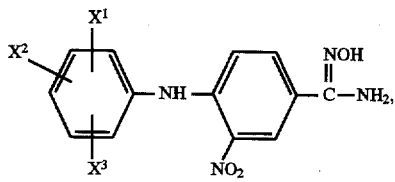

where $X^1$, $X^2$ and $X^3$ are each as defined above, and then reacting the said amide-oxime with the carboxylic acid derivative of the formula VIII.

With the last method, it is of particular advantage to effect the formation of the amide-oxime XI and the reaction with the carboxylic acid derivative VIII in an isobutanol-water mixture and not to intermediately isolate the amide-oxime XI.

Reacting the aldoxime of the formula XI with diketene gives a nitro dye of the formula I where $X^4$ is the radical of the formula

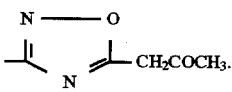

The novel nitro dyes of the formula I are advantageously suitable for dyeing or printing textile materials.

Suitable textile materials are for example polyester in the various make-up forms (for example woven fabric, knitted fabric, yarn or staple) or their blends with other fibers.

It is particularly advantageous to use the nitro dyes of the formula I together with UV absorbers. Suitable UV absorbers are for example those of the formula XII or XIII

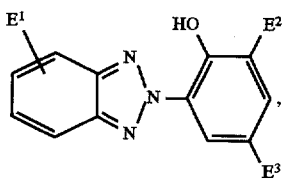

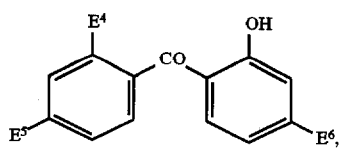

where $E^1$ is hydrogen or chlorine, $E^2$ and $E^3$ are independently of each other hydrogen or $C_1$–$C_8$-alkyl which may be phenyl-substituted, $E^4$ is hydrogen or hydroxyl, and $E^5$ and $E^6$ are independently of each other hydrogen, hydroxyl, or $C_1$–$C_6$-alkoxy which may be substituted by hydroxyl, $C_1$–$C_4$-alkoxy, $C_1$–$C_4$-alkanoyloxy or benzoyloxy.

Of particular suitability are UV absorbers of the formula XIIa, XIIb, XIIIa or XIIIb

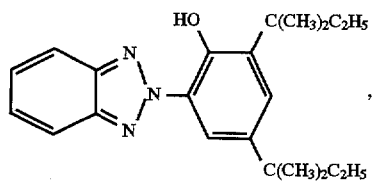

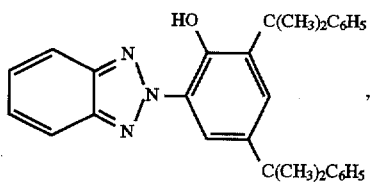

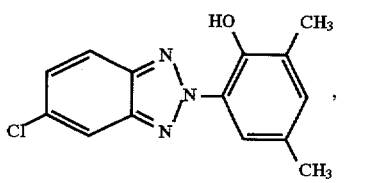

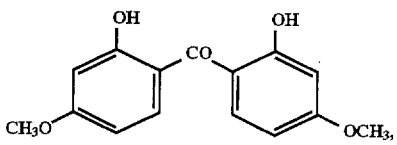

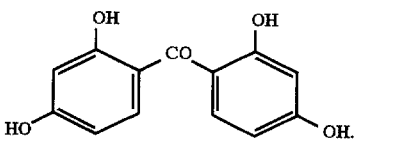

The UV absorbers can be used individually or else in mixture. The mixtures may comprise different species of the formula XII or XIII or else mixtures of compounds of the formulae XII and XIII.

The amount of UV absorber used is generally from 1 to 8% by weight, preferably from 2 to 5% by weight, based on the weight of the nitro dyes.

The nitro dyes of the formula I are notable for an advantageous application property profile. More particularly, they have very good lightfastness at high black-panel temperatures.

The Examples which follow illustrate the invention.

GENERAL DYEING METHOD

This method can be used to apply the dyes more particularly described below.

10 g of polyester fabric are introduced at 50° C. into 200 ml of a dyeing liquor containing 0.5% by weight, based on the polyester fabric, of a dye preparation and whose pH has been adjusted to 4.5 with acetic acid. After 5 min at 50° C. the temperature of the liquor is raised over 30 min to 130° C., held at that temperature for 60 min and then cooled down to 60° C. over 20 min.

Thereafter the dyed polyester fabric is reduction cleared by treating it at 65° C. for 15 min in 200 ml of a liquor containing 5 ml/l of 32% strength by weight sodium hydroxide solution, 3 g/l of sodium dithionite and 1 g/l of an addition product of 48 mol of ethylene oxide with 1 mol of castor oil. Finally the fabric is rinsed, neutralized with dilute acetic acid, rinsed once more and dried.

The abovementioned dye preparation contains 40% by weight of nitro dye and 60% by weight of a dispersant based on ligninsulfonate, in each case based on the weight of the preparation. Based on the weight of nitro dye, the dye preparation may additionally contain from 1 to 8% by weight of a UV absorber more particularly signified above.

EXAMPLE 1 a) 277 g of p-chlorobenzonitrile were stirred in a mixture of 166 g of sodium carbonate, 600 ml of water and 640 ml of isobutanol and also 1 g of a heavy metal complexing agent and 170 g of hydroxylamine sulfate at 90° C. for 5 h. The batch was then allowed to settle at 40° C. and the aqueous phase was discarded. Then the isobutanol phase obtained was admixed with 225 g of acetic anhydride. This was followed by stirring for 30 min, distillative removal of the isobutanol and precipitation with water. The product was isolated and dried at 160° C. Yield: 390 g of the product of the formula

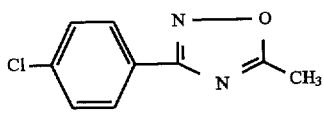

b) 98 g of the product described under a) were dissolved in 250 ml of concentrated sulfuric acid at not more than 20° C. Then 25 ml of 98% strength by weight nitric acid were added dropwise at ≦10° C., and the batch was subsequently stirred for 10 h and poured onto ice-water. Isolation, filtration with suction, washing and drying left 116 g of the product of the formula

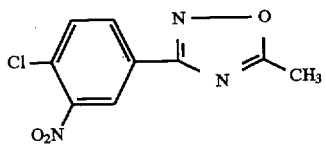

mp.: 110° C.

c) 25 g of the product described under b) were stirred with 70 g of m-toluidine at from 145° to 150° C. for 5 h and then additionally at 160° C. for 2 h. Thereafter the mixture was cooled down to about 100° C. and it was added with stirring to 1000 ml of water and 50 ml of concentrated hydrochloric acid. The precipitated yellow dye of the formula

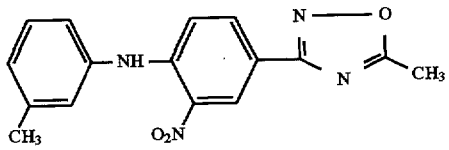

was filtered off with suction and washed with water. Drying left 31 g of an orange powder which, by the dyeing method described at the beginning, dyes polyester fabric in a reddish yellow hue to an excellent fastness level. More particularly, the dye has good exhaustion characteristics even at a temperature as low as 120° C. and an excellent lightfastness. Its absorption maximum in a solution of 0.25 g/liter of 2:1 v/v N,N-dimethylformamide/glacial acetic acid is 432 nm. The extinction coefficient of the crude product at the maximum is about 24.

EXAMPLE 2

196 g of hydroxylamine sulfate were added to a mixture of 685 ml of water and 132 g of sodium carbonate. A complexing agent was added to remove any traces of heavy metal present, followed by a solution of 235 g of benzonitrile in 685 ml of isobutanol. After stirring at the boil for 6 hours the batch was allowed to settle, and the (lower) aqueous phase was removed. Thereafter the organic phase was admixed with 451 g of 3-nitro-4-chlorobenzoyl chloride, dissolved in 1100 ml of anhydrous acetone, and the mixture was stirred at from 30° to 40° C. for 45 min. It was then diluted with 5000 ml of cold water, and the precipitated product was filtered off with suction (mp.: 137° C.). The product was then heated to 190° C. to evaporate off the water, leaving the product of the formula

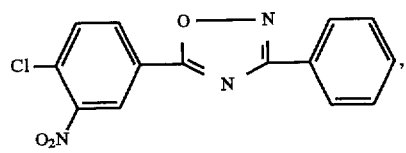

which melts at 146° C. It was reacted with aniline at from 150° to 160° C. similarly to Example 1, giving the orange powder of the formula

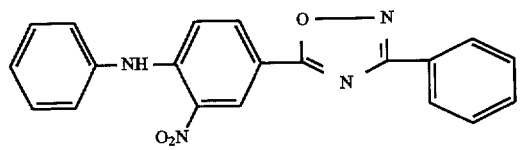

mp.: 216° C.

EXAMPLE 3 a) 183 g of 3-nitro-4-chlorobenzonitrile were admixed with 320 ml of isobutanol, 300 ml of water, 108 g of sodium carbonate and 0.5 g of a heavy metal complexing agent, and the mixture was stirred at 80° C. for 5 h. Thereafter the mixture was allowed to settle, the aqueous phase was separated off. The organic phase was then admixed with 90 g of sodium bicarbonate, followed by 155 g of benzoyl chloride, and subsequently stirred at from 60° to 90° C. for 30 min. Then 250 ml of water were added, the mixture was allowed to settle, and then the aqueous phase was again separated off. The organic phase was distilled to remove isobutanol, the residue being heated to 170° C. A customary workup left 290 g of the product of the formula

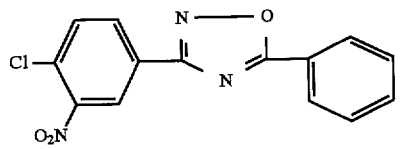

mp.: 141° C.

b) 302 g of the product described under a) were admixed with 180 g of m-xylidine, a catalytic amount of copper powder and 60 g of N-methylpyrrolidone. The mixture was then heated to 130° C., 55 g of sodium carbonate were added over 1 h. At the end the temperature was raised to 165° C. Thereafter the batch was cooled down to 100° C. and then adjusted with dilute hydrochloric acid to pH 2. The precipitated dye of the formula

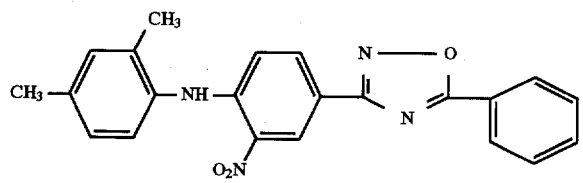

was filtered off with suction and washed with water.

This left 380 g of an orange powder, mp.: 143° C.

The dye gives a yellow solution in acetone and dyes polyethylene terephthalate fabric in a deep yellow shade. The dyeings have excellent lightfastness at high black-panel temperatures, and the dye shows good dyeing characteristics.

The same method can be used to obtain the yellow dyes listed below.

| Ex. No. | |
|---|---|
| 4 | 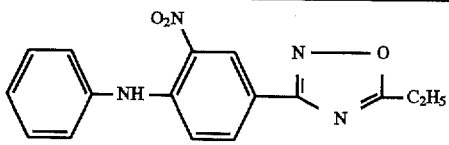 |
| 5 | 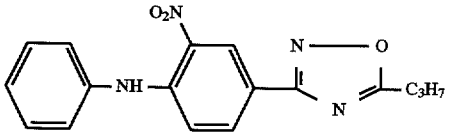 |
| 6 | 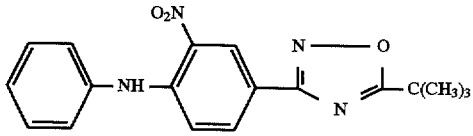 |
| 7 | 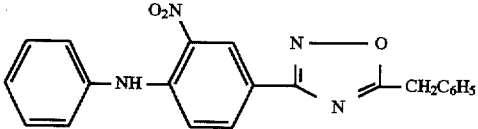 |
| 8 | 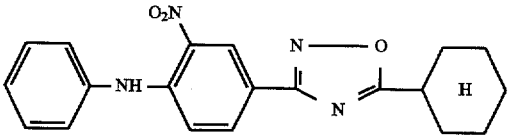 |
| 9 | 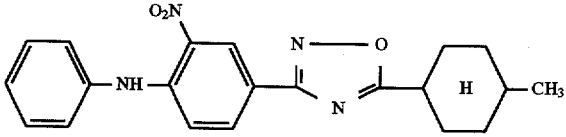 |
| 10 | 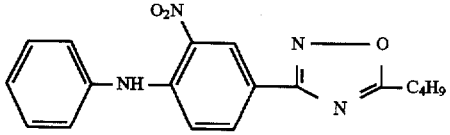 |
| 11 | 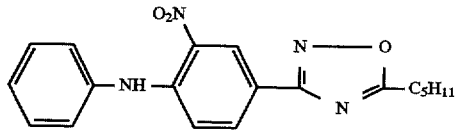 |
| 12 | 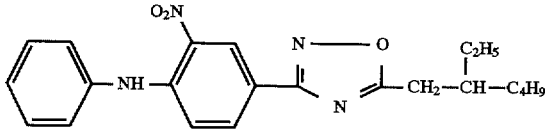 |

-continued
| Ex. No. | |
|---|---|
| 13 | 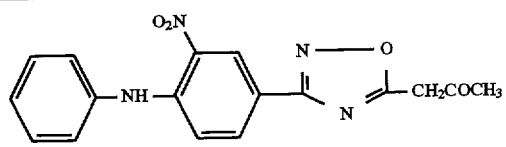 |
| 14 | 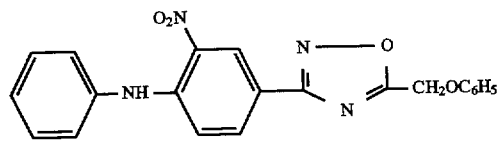 |
| 15 | 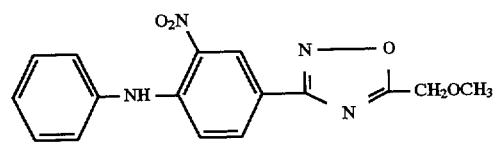 |
| 16 | 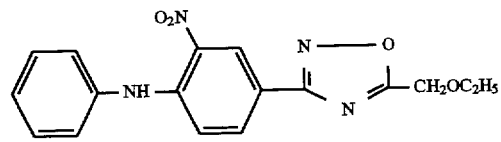 |
| 17 | 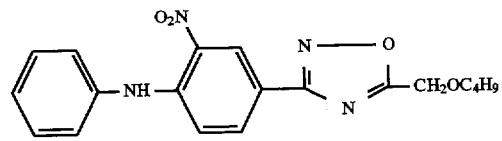 |
| 18 | 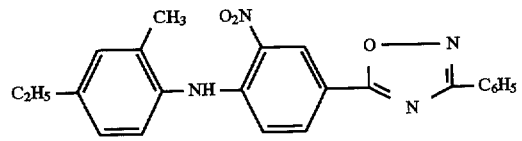 |
| 19 | 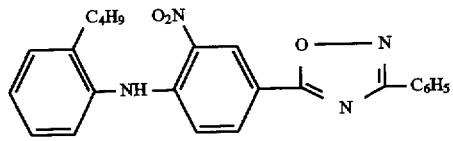 |
| 20 | 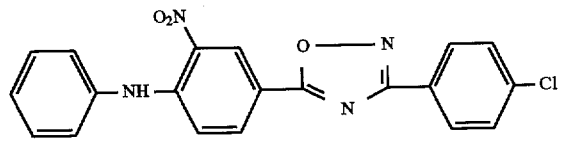 |
| 21 | 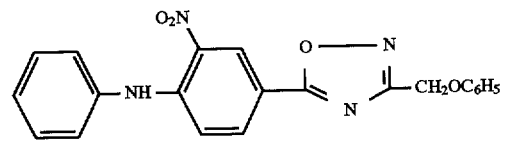 |
| 22 | 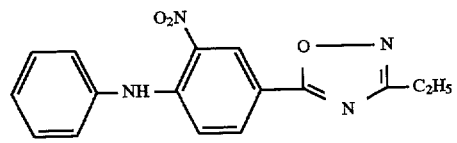 |

-continued
| Ex. No. | |
|---|---|
| 23 | 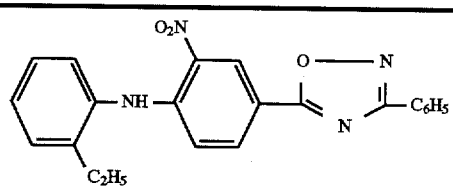 |
| 24 | 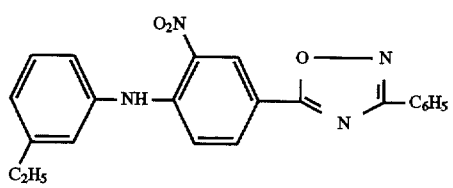 |
| 25 | 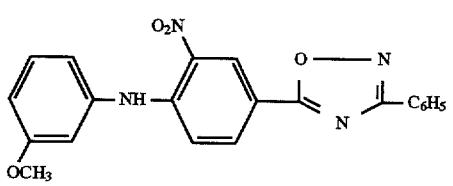 |
| 26 | 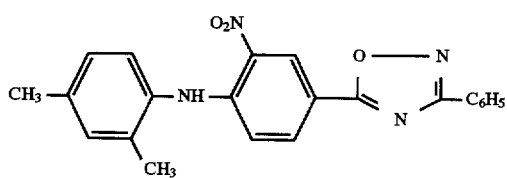 |
| 27 | 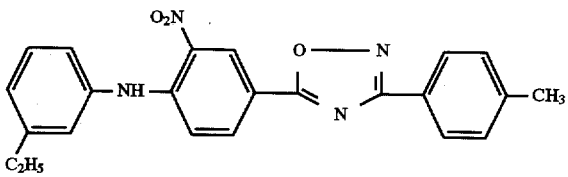 |
| 28 | 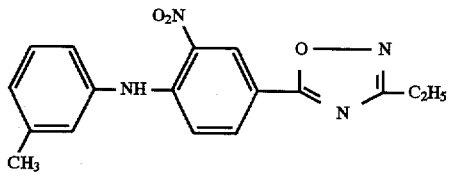 |
| 29 | 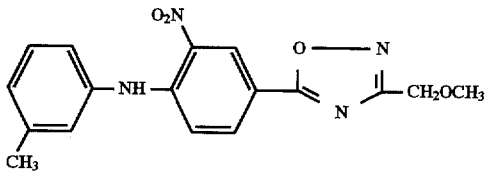 |
| 30 | 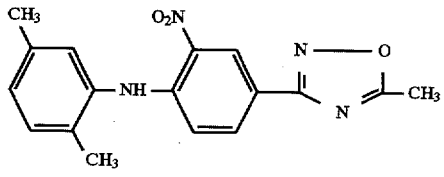 |
| 31 | 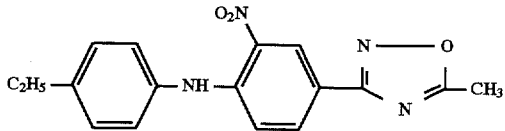 |

-continued
| Ex. No. | |
|---|---|
| 32 | 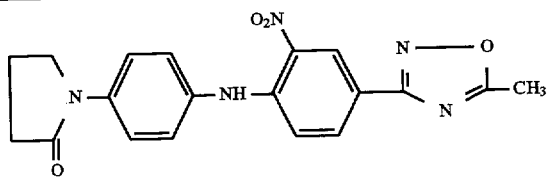 |
| 33 | 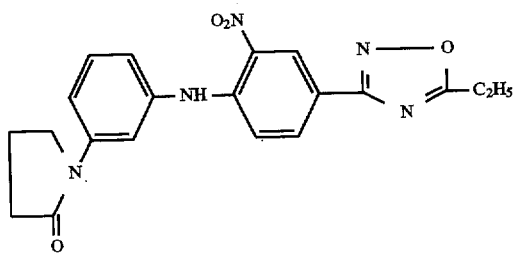 |
| 34 | 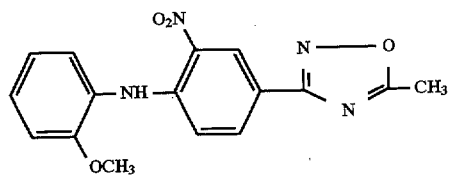 |
| 35 | 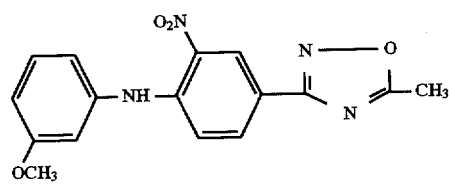 |
| 36 | 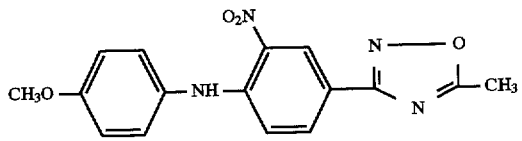 |
| 37 | 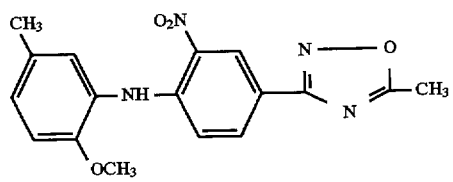 |
| 38 | 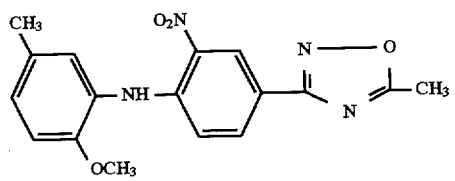 |
| 39 | 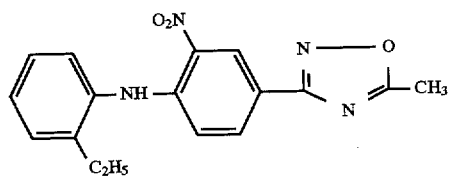 |

| Ex. No. | |
|---|---|
| 40 | 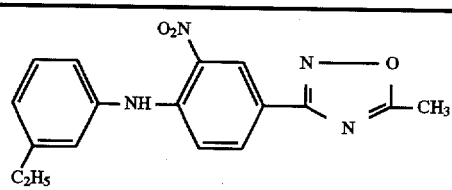 |
| 41 | 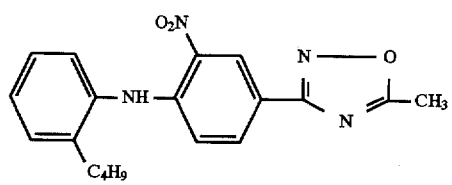 |
| 42 | 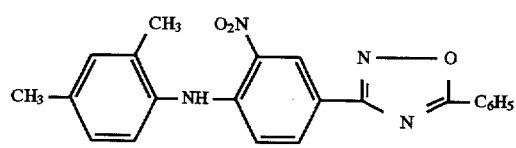 |
| 43 | 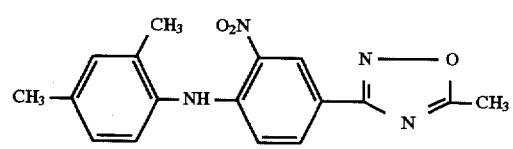 |
| 44 | 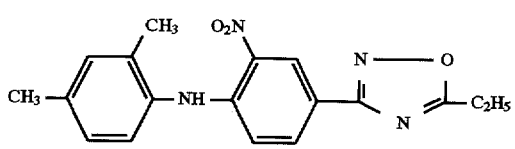 |
| 45 | 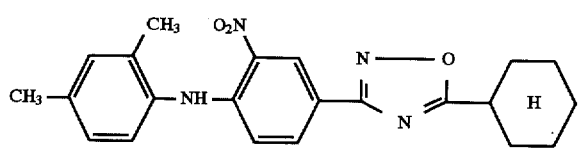 |
| 46 | 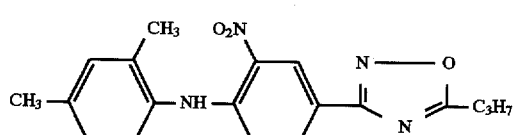 |
| 47 | 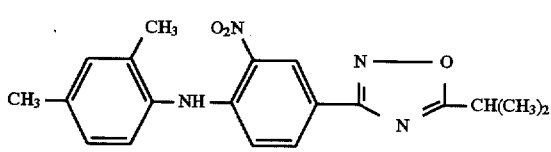 |
| 48 | 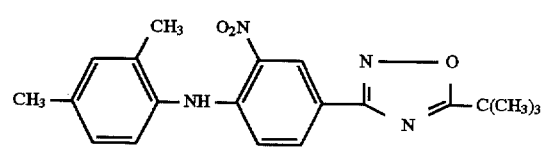 |
| 49 | 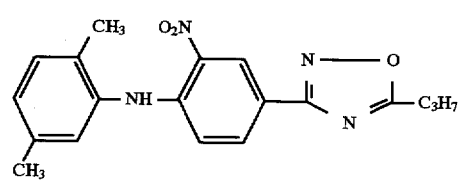 |

-continued
| Ex. No. | |
|---|---|
| 50 | 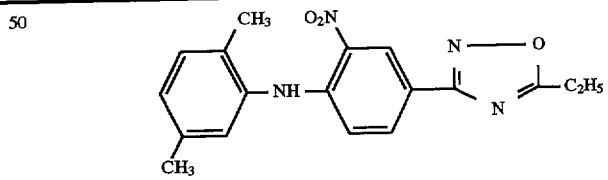 |
| 51 | 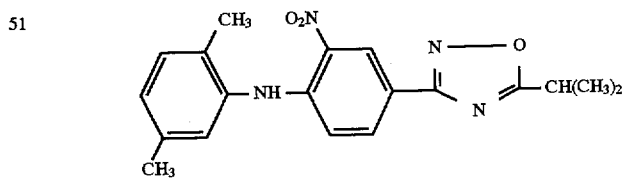 |
| 52 | 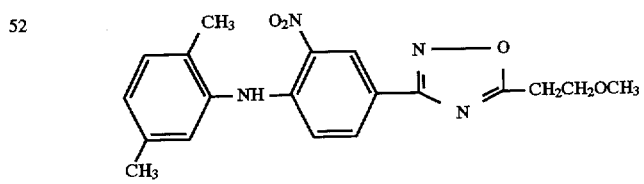 |
| 53 | 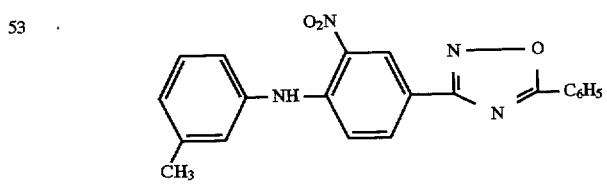 |
| 54 | 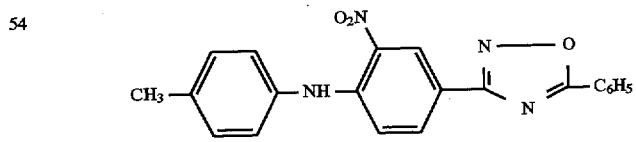 |
| 55 | 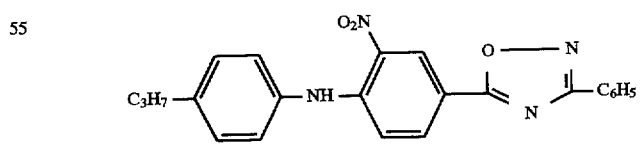 |
| 56 | 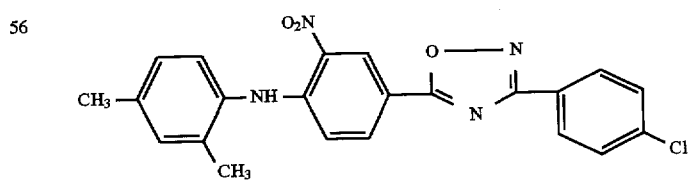 |
| 57 | 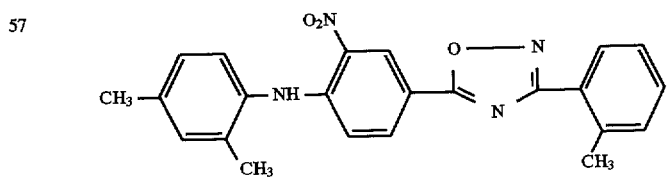 |
| 58 | 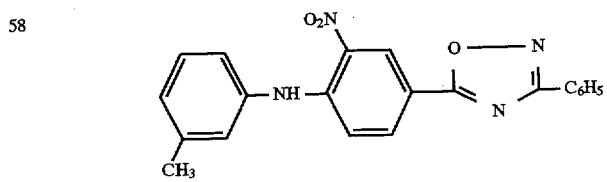 |

-continued
| Ex. No. | |
|---|---|
| 59 | 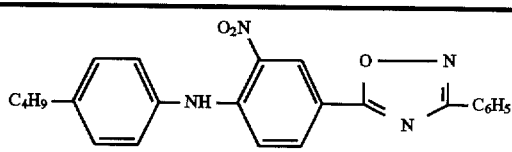 |
| 60 | 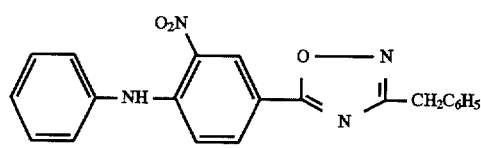 |
| 61 | 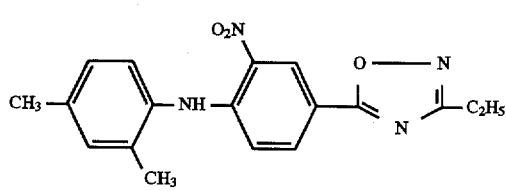 |
| 62 | 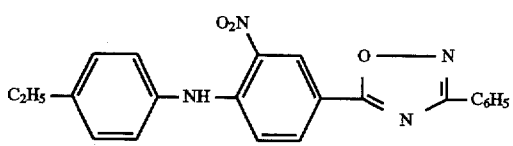<br>(mp.: 139° C.) |
| 63 | 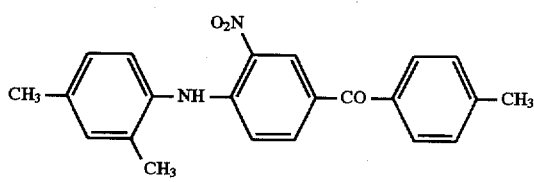 |
| 64 | 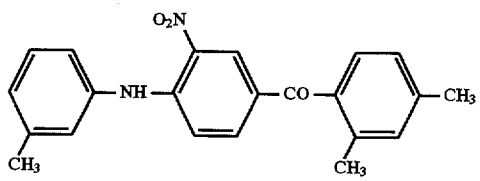 |
| 65 | 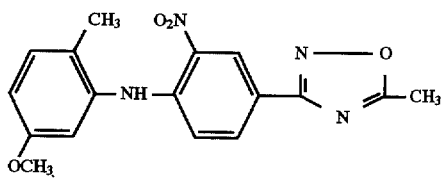 |
| 66 | 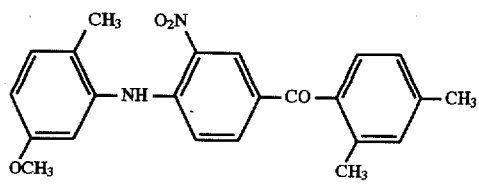 |

We claim:
1. A nitro dye of formula I:

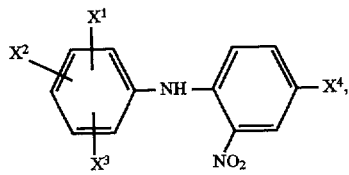

wherein

X$^1$ and X$^2$ are independently of each other hydrogen, C$_1$–C$_6$-alkyl, C$_1$–C$_6$-alkoxy or pyrrolidin-2-on-1-yl, X$^3$ is hydrogen or C$_1$–C$_6$-alkyl, and X$^4$ is a radical of the formula

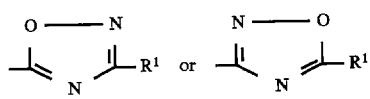

wherein R$^1$ is hydrogen, C$_1$–C$_{12}$-alkyl optionally interrupted by from 1 to 3 oxygen atoms in ether function and optionally substituted by phenyl, phenoxy or acetyl, C$_3$–C$_7$-cycloalkyl, which is optionally substituted by C$_1$–C$_4$-alkyl, or phenyl, which optionally is substituted by C$_1$–C$_4$-alkyl-, C$_1$–C$_4$-alkoxy- or halogen.

2. Nitro dyes as claimed in claim 1 wherein X$^1$ and X$^2$ are independently of each other hydrogen or C$_1$–C$_4$-alkyl and X$^3$ is hydrogen.

3. Nitro dyes as claimed in claim 1, wherein X$^4$ is a radical of the formula

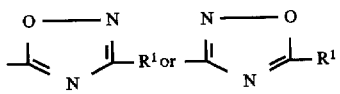

where R$^1$ is in each case as defined in claim 1.

4. Nitro dyes as claimed in claim 1, wherein X$^4$ is a radical of the formula

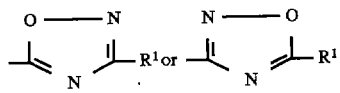

where R$^1$ is in each case C$_1$–C$_4$-alkyl, cyclohexyl or phenyl.

5. Nitro dyes as claimed in claim 1, of the formula Ia

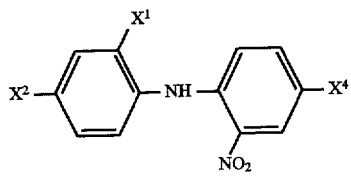

where X$^1$, X$^2$ and X$^4$ are each as defined in claim 1.

6. Nitro dyes as claimed in claim 5 where X$^1$ and X$^2$ are both hydrogen or both methyl and X$^1$ is hydrogen and X$^2$ is C$_1$–C$_4$-alkyl.

7. A process for preparing the nitro dyes of claim 1, which comprises reacting a nitrobenzene of the formula II

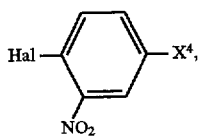

where Hal is halogen and X$^4$ is as defined in claim 1, with anilines of the formula III

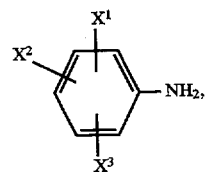

where X$^1$, X$^2$ and X$^3$ are each as defined in claim 1.

8. A process for preparing nitro dyes as claimed in claim 1 of the formula I where X$^4$ is a radical of the formula

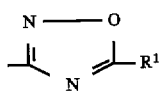

which comprises converting a cyano compound of the formula X

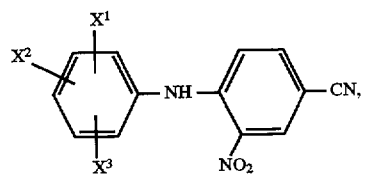

where X$^1$, X$^2$ and X$^3$ are each as defined in claim 1, with hydroxylamine into the amide-oxime of the formula XI

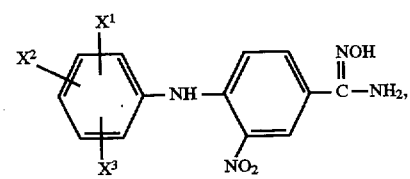

where X$^1$, X$^2$ and X$^3$ are each as defined in claim 1, and then reacting said amide-oxime with a carboxylic acid derivative of the formula VIII

R$^1$—CO—Z    (VIII), where Z is halogen, C$_1$–C$_6$-alkoxy or a radical of the formula O—CO—R$^1$ and R$^1$ is in each case as defined in claim 1, the reaction being carried out in an isobutanol-water mixture without intermediately isolating the amide-oxime of the formula XI.

9. A method of dyeing or printing a textile material, comprising: dyeing or printing a textile material with a nitro dye of formula I:

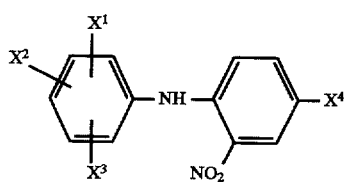 (I)

wherein

X¹ and X² are independently of each other hydrogen, $C_1$–$C_6$-alkyl, $C_1$–$C_6$-alkoxy or pyrrolidin-2-on-1-yl, X³ is hydrogen or $C_1$–$C_6$-alkyl, and X⁴ is a radical of the formula

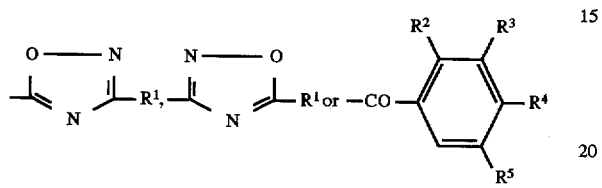

wherein R¹ is hydrogen, $C_1$–$C_{12}$-alkyl optionally interrupted by from 1 to 3 oxygen atoms in ether function and optionally substituted by phenyl, phenoxy or acetyl, $C_3$–$C_7$-cycloalkyl, which optionally is substituted by $C_1$–$C_4$-alkyl, or phenyl, which optionally is substituted by $C_1$–$C_4$-alkyl-, $C_1$–$C_4$-alkoxy- or halogen, R² and R³ are independently of each other hydrogen, $C_1$–$C_6$-alkyl or $C_1$–$C_6$-alkoxy, R⁴ is hydrogen, methyl, ethyl, methoxy or ethoxy, and R⁵ is hydrogen or $C_1$–$C_6$-alkyl.

* * * * *